United States Patent [19]

Moling

[11] Plant 4,285

[45] Jul. 25, 1978

[54] CHERRY PLUM BUSH

[76] Inventor: LeRoy I. Moling, Rte. 3, Fergus Falls, Minn. 56537

[21] Appl. No.: 781,333

[22] Filed: Mar. 25, 1977

[51] Int. Cl.[2] ..... A01H 5/03

[52] U.S. Cl. ..... Plt./38

[58] Field of Search ..... Plt./37, 38

*Primary Examiner*—Robert E. Bagwill
*Assistant Examiner*—James R. Feyrer
*Attorney, Agent, or Firm*—Leo Gregory

[57] ABSTRACT

A Cherry-Plum Plant characterized in being a bush, having rapid early growth with a spread substantially equal to height, having tough flexible stems and branches which bear a heavy fruit load without breaking, being very disease resistant and able to withstand severe cold weather without cover. The fruit is distinctive in having a small pit and small cavity, being substantially freestone, having relatively thick flesh almost free of astringency, being sweet in taste, having a smooth texture and being excellent for eating and canning and being very hardy. The fruit clings to the bush even when fully ripe in the face of strong winds.

3 Drawing Figures

BACKGROUND OF THE INVENTION

For many years I have been engaged in a plant breeding program at my orchard located at Route 3, Fergus Falls, Minn. 56537. My new variety described herein resulted from such effort.

My new variety of Cherry-Plum Bush originated as a seedling from open pollination and having unknown parentage. Some Sapalta bushes were growing some distance away and these died by the time of my discovery. There were some suckers growing in the area of my bushes where previously some unknown varieties of cherry bushes had grown and died. What particularly led me to my discovery was the unusually sweet and delicious taste of the fruit. The fruit has a distinctive reddish purple color, it has but a small cavity, it is substantially freestone and has relatively thick flesh.

My bush is distinguished from the Sapalta by being a more vigorous bush and having a greater disease and cold resistance and in having a fruit which is more disease resistant and which has a thicker flesh, a smaller pit and cavity and unlike the Sapalta it is almost astringent-free.

I asexually reproduced my new variety by grafting short stem buds having several buds each in the spring and by grafting single buds in the fall with the grafts being onto wild plum root stocks. Upon maturity my reproductions ran true to the parent bush.

DESCRIPTION OF THE DRAWINGS

The drawings are illustrations by photographic reproduction in color as follows.

DESCRIPTION OF THE NEW VARIETY

Figure 1:
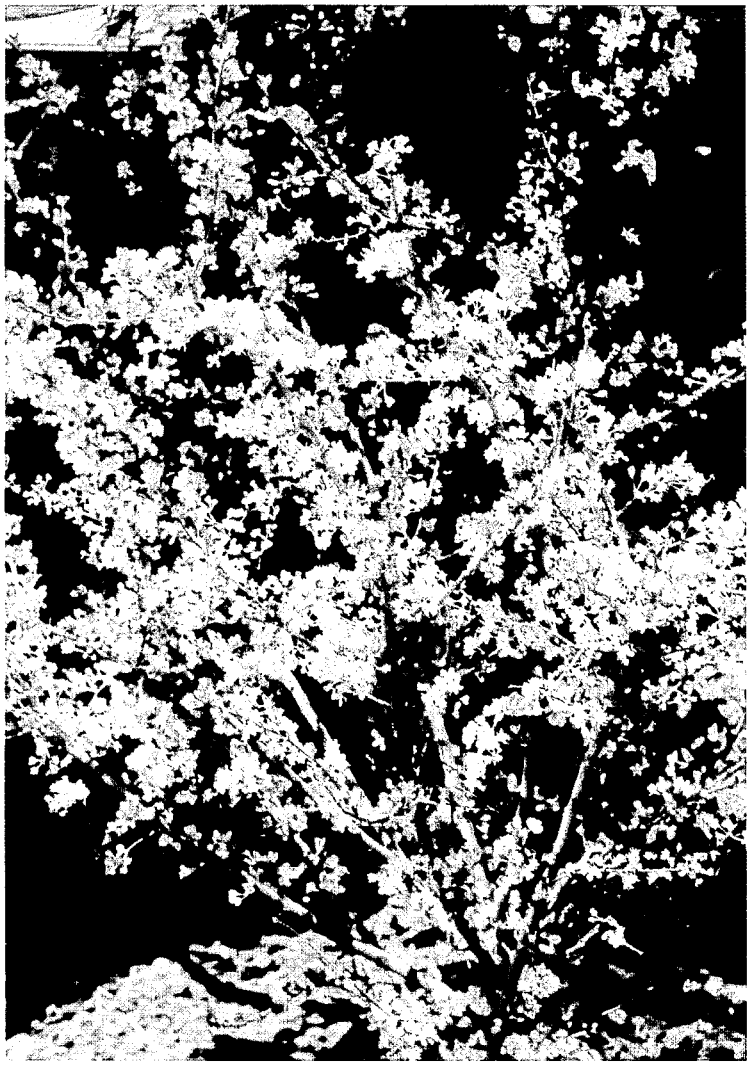
FIG. 1 is a view of a three year old bush in blossom.
Figure 2:
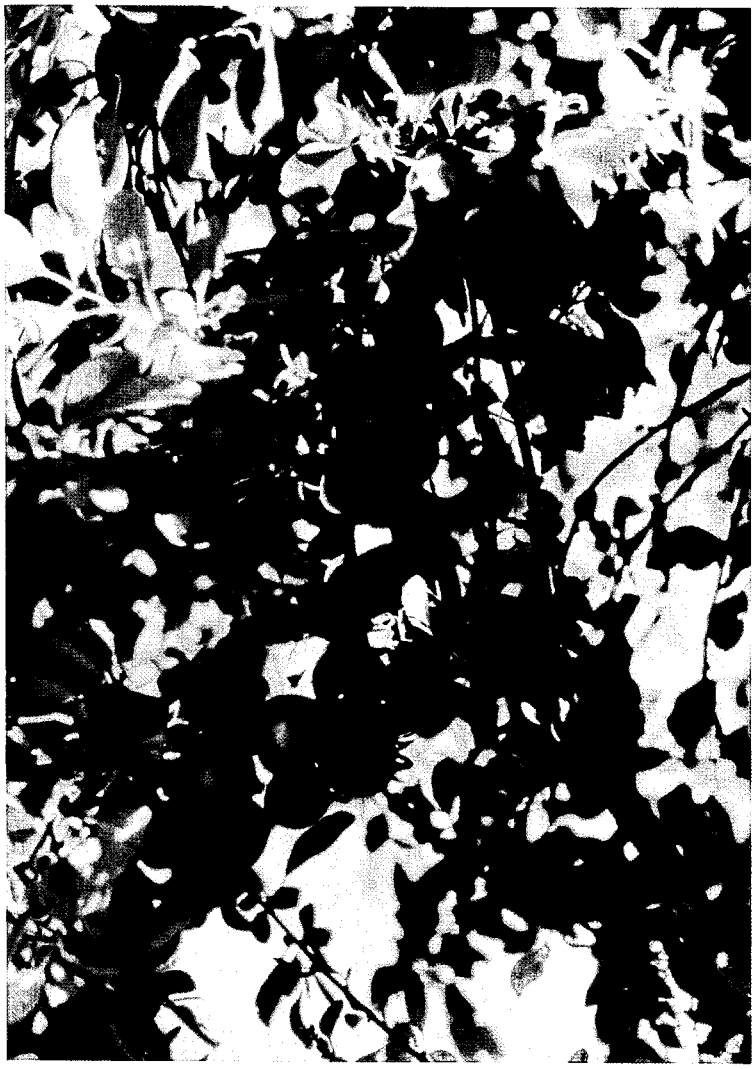
FIG. 2 is a view of the limb of a three year old bush with ripe fruit thereon.
Figure 3:
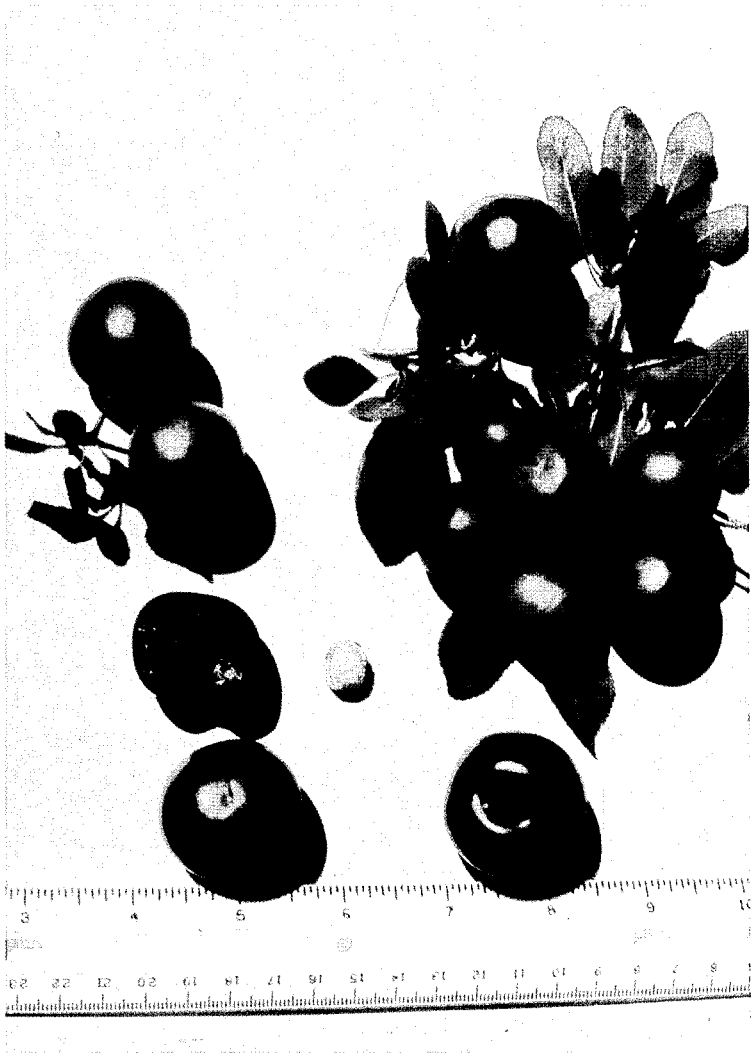
FIG. 3 is a view of a cluster of fruit with one fruit shown halved to indicate flesh thickness with a pit along side thereof.

The following is a detailed description of my new variety of Cherry-Plum Bush based upon my observations of specimens grown at rural Fergus Falls, Minn.

Color terminology is in accordance with the Royal Horticulture Society of London Colour Chart except where general color terms of ordinary dictionary significance are obvious. The color comparisons are as close as could be made comparing colored photographs to the R.H.S. Colour Chart.

Growth Habit:

Starting as a bud in the spring, a bush will grow approximately 3½ feet the first year. A growth of 5½ feet is attained within 3 years. The bush starts out at a width substantially equal to its height with numerous fruit bearing stems and branches and has vigorous growth with a prolific formation of fruit clusters. Fruiting begins the next growing season.

Within a year, the stem growth is approximately ⅝ inch in diameter with branches 1/16 to ¼ inch in diameter extending up to a length of 24 inches. The branches are spaced fairly evenly. Every stem and branch is loaded with fruit buds. At the base of each branch there is a whorl of several fruit buds.

While a set of fruit buds are developing fruit, the buds will also start two types of new growth. One type of new growth will be a short stem or knob about ⅛ inch in diameter with a length from ¼ to ¾ inch and the same will have numerous fruit buds on the order of 9 to 13. The second type of new growth will be a spur-like stem approximately 1/16 to ⅛ inch in diameter up to a length on the order of 6 inches and said stems are loaded with sets of buds spaced ⅜ to ⅝ inch apart. Many sets of buds comprise clusters of three fruit buds and one leaf bud. Each fruit node opens from two to five blossoms.

While the Plum-Cherry Bush is developing, it generally grows one leaf a day on each stem or branch with a corresponding growth of fruit buds following later in the season.

The second and third year growth of my Cherry-Plum Bush is approximately 12 inches a year.

Bush:

*Size.*—Medium.

*Vigor.*—Vigorous.

*Growth.*—Upright spreading and a mature specimen in the Fergus Falls area would attain a width substantially equal to height, the same being on the order of 5½ feet.

*Production.*—Heavy crop load, very productive.

*Bearing.*—Uniform crop production from year to year. No thinning necessary.

*Resistance.*—1. Very disease and insect resistant. Requires no spraying. 2. Cold resistant — can stand temperature down to −40° F without cover.

Stems and branches:

*Size.*—Small, tough and flexible. Bears a heavy crop load without breaking.

*Texture.*—Medium.

*Bark.*—Smooth. Starts to turn grey in the first year. During the second and third year it turns uniformly gray (Gray White Group plate 156D).

*Stem.*—Several, approximately $\frac{5}{8}$ inch in diameter, no central leader.

*Branches.*—From 1/16 to $\frac{1}{4}$ inch in diameter to approximately 24 inches in length.

Leaves:

*Generally.*—Alternate, ovate and finely serrate.

*Size.*—On new growth on the order of $2\frac{1}{4}$ inches long and $1\frac{1}{2}$ inches wide. On old growth on the order of $1\frac{1}{4}$ inches long and $\frac{5}{8}$ inch wide.

*Color.*—Upper side olive green (Green Group plate 133B). Lower side — lighter shade of green (Green Group plate 128C).

*Spacing.*—Generally — Leaves are approximately $\frac{3}{4}$ inch apart.

Leaf buds:

*Generally.*—Small and round from 1/32 to 1/16 inch in diameter.

Fruit buds:

*Generally.*—Each fruit bud opens from two to five flower buds. At the base of every branch is a whorl of several fruit buds.

Flowers:

*Shape.*—Round and showy, open to approximately $\frac{5}{8}$ inch in diameter.

*Petalage.*—Five petals.

*Form.*—Cupped.

*Color.*—Open flower is white (White Group plate 155D).

Fruit ripening data:

*Blooming.*—Approximately from May 20 to June 10.

*Ripening.*—Generally from August 10 to August 20 in rural Fergus Falls, Minn.

Maturity:

*Growth.*—The fruit appears to double in size during the last two weeks of its ripening period.

*Clinging.*—Even when fully ripe the fruit clings securely to the stem or branch even in the face of a heavy wind.

*Size.*—Almost round with the axial diameter from 1 to $1\frac{1}{4}$ inches.

Skin:

*Color.*—Dark reddish purple (Purple Group plate 59A) with a small cluster of dull brown speckles on the sun side.

*Quality.*—Thin and tender and almost free of astringency. There is a tendency to split if there is an excess of moisture during ripening period.

Flesh:

*Juice.*—Abundant. Has a dark reddish purple color (Purple Group plate 59A).

*Generally.*—The fruit has a relatively small cavity with thick flesh of a smooth texture free of fibers.

*Flavor.*—Delicate, sweet and aromatic.

*Eating quality.*—Excellent.

*Canning quality.*—Excellent.

Pit:

*Size.*—Small, slightly elongated but substantially round. From $\frac{1}{4}$ to $\frac{3}{8}$ inch in diameter.

*Surface.*—Substantially smooth.

Fruit stem:

*Length.*—From $\frac{1}{2}$ to $\frac{7}{8}$ inch.

Use:

*Generally.*—For market, eating and canning.

Keeping quality:

*Generally.*—Very good.

Resistance:

*Generally.*—Very disease resistant and requires no spraying.

Ripening:

*Generally.*—The fruit appears to ripen from its cavity outwardly. Before fully ripening the flesh is dark red while the skin is still a greenish unripe color. When ripe, the flesh and skin are a dark reddish purple color throughout (Purple Group 59A).

*Appearance.*—The outer surface is uniform and free of markings except that at the underside is a small indentation with three radial lines, of which one is extended.

The Cherry-Plum Bush described herein may vary in slight detail due to the soil and climate conditions under which the variety may be grown; the present description being of my variety grown in the Fergus Fall area in West Central Minn.

I claim:

1. I claim a new and distinctive variety of a Cherry-Plum Bush substantially as herein shown and described characterized particularly as to novelty by the unique combination of a relatively short widespread growth of a bush having tough flexible stems and branches, able to bear a heavy fruit load and having fruit buds approximately every $\frac{3}{8}$ to $\frac{5}{8}$ inch along all of the stems and branches and a cluster of buds at the base of each branch, being very disease and insect resistant and able to withstand frigid temperatures without cover and having a rapid growth producing a first crop in the growing season following grafting, the fruit being substantially freestone, having a small pit and cavity and having a relatively thick, sweet, smooth, textured fruit; the variety — which resembles the "Sapalta" Cherry Plum — being distinctively characterized, in comparison, by fruit which has thicker flesh, a smaller pit, and by being almost free of astringency.

* * * * *